United States Patent [19]

Yamawaki et al.

[11] 4,111,039

[45] Sep. 5, 1978

[54] APPARATUS FOR MEASURING THE HARDNESS OF RUBBER

[75] Inventors: Takeshi Yamawaki, Hiratsuka; Tokitaro Hoshijima, Yokohama; Kiichiro Aga, Machida, all of Japan

[73] Assignee: Mitsubishi Kasei Kogyo Kabushiki Kaisha, Japan

[21] Appl. No.: 751,478

[22] Filed: Dec. 16, 1976

[30] Foreign Application Priority Data

Dec. 19, 1975 [JP] Japan .................................. 50-151391

[51] Int. Cl.² .......................... G01N 3/42; G01N 3/48
[52] U.S. Cl. ........................................... 73/81; 73/82
[58] Field of Search ................................ 73/81, 82, 78

[56] References Cited
U.S. PATENT DOCUMENTS

| | | | |
|---|---|---|---|
| 1,581,839 | 4/1926 | Dahlqvist | 73/82 |
| 3,421,364 | 1/1969 | Moneypenny et al. | 73/82 |
| 3,498,114 | 3/1970 | Garber et al. | 73/82 |

Primary Examiner—Anthony V. Ciarlante
Attorney, Agent, or Firm—Oblon, Fisher, Spivak, McClelland & Maier

[57] ABSTRACT

In apparatus for measuring the hardness of rubber of the type wherein a needle is urged against the surface of a rubber sample and the degree of penetration of the needle is measured there are provided a coil spring, a lever for causing the needle to compress the spring and a releasable latch for holding the spring in the compressed state. When the spring is released it urges the needle against the rubber sample under a prescribed speed and force. The displacement of the needle is detected by an electric transducer and its output signal is processed by an electric circuit including a peak detector and an analogue-digital converter for digitally displaying the displacement. When the spring is released a switch is operated to start the analogue-digital converter for determining the starting point of the time necessary to measure the displacement by using the time as a parameter.

1 Claim, 4 Drawing Figures

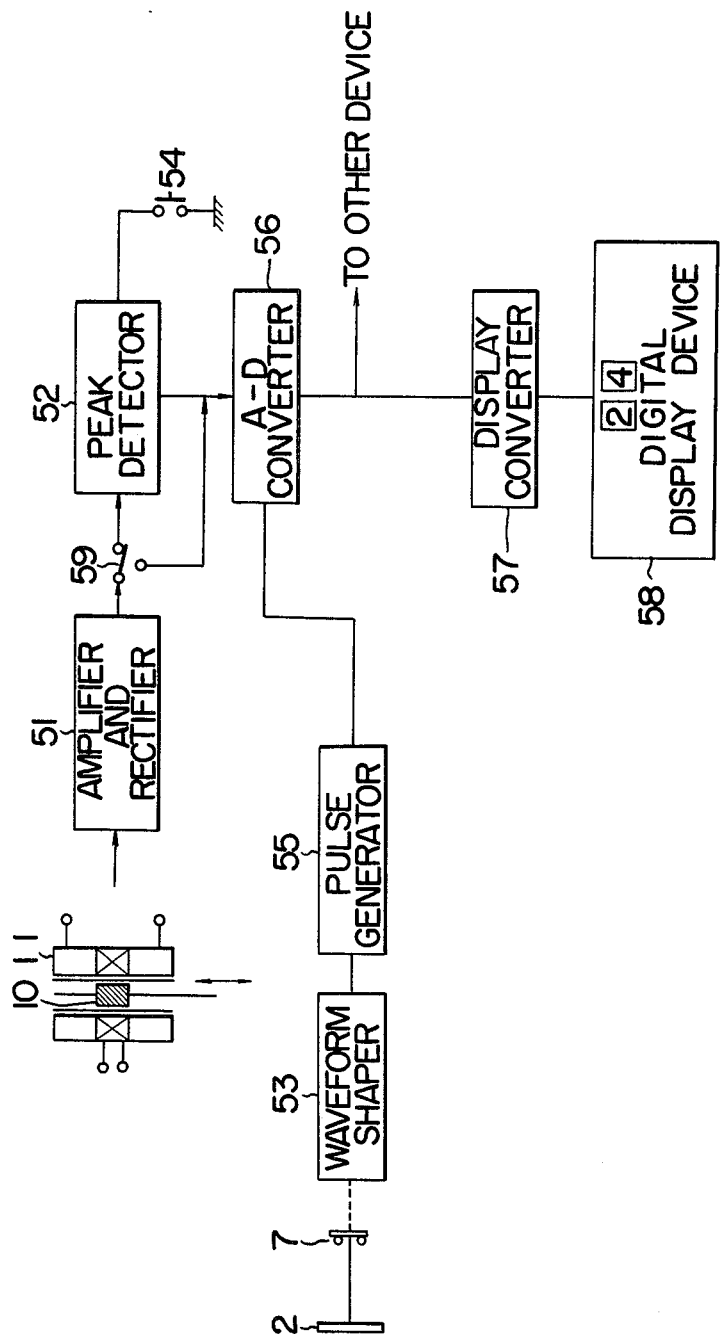

APPARATUS FOR MEASURING THE HARDNESS OF RUBBER

BACKGROUND OF THE INVENTION

This invention relates to apparatus for measuring the hardness of rubber, or a hardness meter, of the type wherein a needle or an indentor is urged against the surface of a sample of rubber and the penetration depth of the needle is measured to determine the hardness of the sample.

The hardness meter of the type just described is constructed such that when a pressing plate having an opening for passing the needle is urged against the surface of the sample, a needle having a prescribed dimension determined by a regulation, for example JIS (Japanese Industrial Standard) K 6301, is urged against the surface of the sample, that the spring pressure is proportioned such that when the displacement of the needle is zero a definite load will be applied to the needle so that the distance between the pressing plate and the end of the needle is proportional to the load applied to the end of the needle, and that the distance over which the needle is pressed back by the surface of the sample is graduated in terms of hardness which is inversely proportional to the hardness.

In operation, the tester is maintained upright and the pressing plate is urged against the surface of the sample while maintaining the needle at right angles with respect thereto so as to determine the hardness of the sample by reading the scale. According to said JIS, the scale is to be read immediately after contacting the pressing plate against the sample. According to (American Standard of Testing Materials) the scale is to be read within one second after contacting the pressing plate or the maximum value should be read, whereas according to DIN (Deutsche Industrie-Norm) the scale should be read after 3 seconds after contacting the pressing plate.

The shape and thickness of the sample are also prescribed by regulations.

In the hardness test of rubber there are the following problems.

1. Since the hardness meter is manually contacted against the surface of the rubber sample the speed and force of urging the needle are not constant thus degrading the test result.

2. When reading the scale, as the pointer moves slowly immediately after contacting the hardness meter against the surface of the sample, the accuracy of the reading varies depending upon the response speed and the skill of the reader.

Thus, measurement errors and personal errors are caused by the method of penetrating the needle and the time of reading the displayed value.

SUMMARY OF THE INVENTION

It is an object of this invention to provide an improved apparatus for measuring the hardness of rubber having a high reliability and capable of eliminating various errors described above.

To attain this object, we have invented novel measuring apparatus in which means is provided for urging the needle against the surface of a sample at a predetermined speed and force and for maintaining the reaction of the sample acting upon the needle at a constant value and for alleviating the reaction thereby increasing the accuracy of measurement. Further, instead of directly reading the movement of the needle as in the prior art apparatus, the movement is detected by an electric transducer and processed by an electric circuit thereby eliminating the errors caused by reading a moving pointer and by the skill of the operator.

According to this invention, there is provided apparatus for measuring the hardness of rubber of the type wherein a needle is urged against the surface of a rubber sample and the degree of penetration of the needle is determined for measuring the hardness, said apparatus comprising driving means for urging the needle against the surface under a predetermined constant speed and force, said driving means including spring means for driving the needle, a lever for causing the needle to store energy in the spring means, and releasable latch means for latching the needle in a position in which the spring means has stored the energy and for releasing the needle to cause the spring means to urge the needle against the surface of the sample, an electric transducer for detecting the degree of penetration of the needle into the sample thereby producing an electric signal corresponding to the displacement of the needle at any time, or the maximum displacement of the needle, and an electric circuit for processing the electric signal.

Where it is desired to measure the displacement by using time as a parameter, a switch is provided to generate a signal when the needle is released, and the signal is applied to the electric circuit for determining the starting point of the time necessary to measure the displacement.

BRIEF DESCRIPTION OF THE DRAWINGS

In the accompanying drawings:

FIG. 4 is a block diagram showing one example of a displacement measuring device.

DESCRIPTION OF THE PREFERRED EMBODIMENT

Samples of various types of rubbers such as natural rubber, stylene-butadiene rubber, butadiene rubber, EPDM (ethylene-propylene diene methylene linkage terpolymer) chloroprene rubber, nitrile rubber, silicone rubber and mixtures thereof can be measured by the apparatus of this invention.

Although the shape of the sample is not limited to any particular shape a sheet having a thickness above a certain value is desirable.

Figure 1:
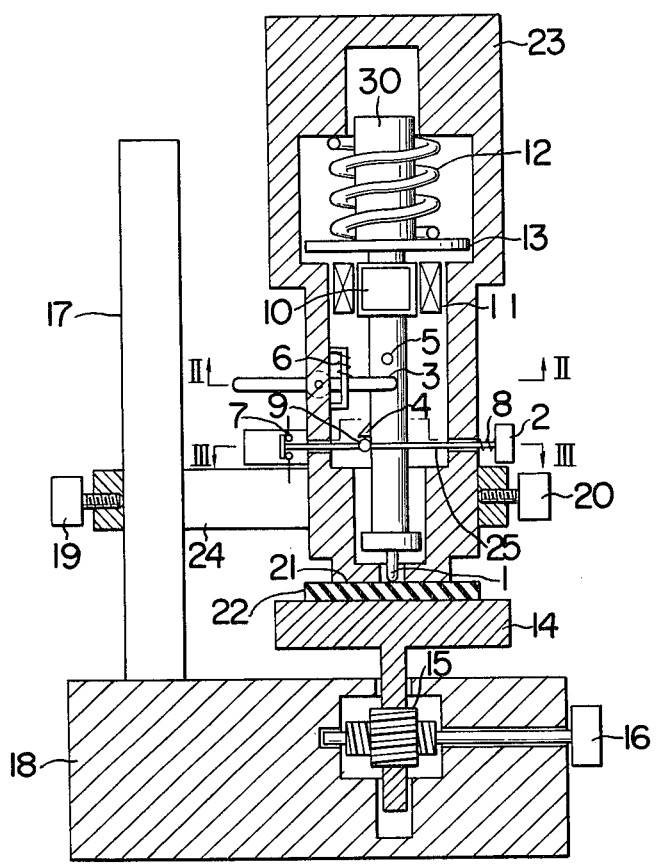
FIG. 1 is a longitudinal sectional view showing one embodiment of this invention.
Figure 2:
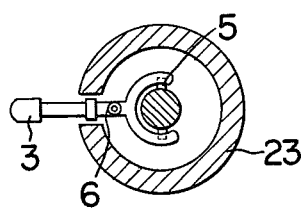
FIGS. 2 and 3 are sectional views of the apparatus shown in FIG. 1 taken along lines II—II and III—III respectively.
Figure 3:
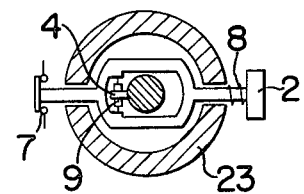

A preferred embodiment of this invention shown in FIGS. 1, 2 and 3 comprises a cylindrical casing 23 mounted on a base 18 by a vertical post 17 and a horizontal frame 24 which is adjustably secured to the post and the casing respectively by set screws 19 and 20. A rubber sample 21 to be measured is mounted on a stationary table 14. The vertical position of the casing 23 is adjusted by set screws 19 and 20 so as to contact the bottom surface 21 of the casing against the upper surface of the sample.

Instead of adjusting the casing 23 in the vertical position it is also possible to hold the casing at a fixed position and to adjust the height of table 14. In the following description the former case will be described.

A needle 1 for measuring the hardness of the sample is secured to or made integral with a holder 30 which is biased against the surface to the sample by a compression coil spring 12 having a predetermined spring constant and acting upon the flange 13 of the needle holder 30. The displacement of the needle is converted into an electric signal by a transducer comprising a magnetic member 10 secured to the holder 30 and a coil 11 surrounding the magnetic member 10, for example. Such transducer may also comprise a Hall element mounted on the needle holder and a stationary magnetic member. Before measurement, the table 14 is lowered to the lowermost position by a dial wheel 16 through a worm gearing 15. Further, the needle and its holder are moved in direction to compress the spring 12 by a bifurcated lever 3 pivotally mounted on the casing 23 and lateral pins 5 secured to the holder 30. Under these conditions the needle holder 30 is held in the raised position by the engagement of a projection 4 of the holder with a latch 9 secured to a push button 2 which is biased by a spring 8, thereby holding the end of the needle 1 in the bottom plane 21 of the casing, that is the surface of the sample 22. Then, the lever 3 is disengaged from pin 5 by a spring 6 as shown in FIG. 1. Accurate position of the end of the needle can be adjusted by adjusting screws, not shown, secured to the bottom surface of the casing 23. Concurrently with this setting of the needle, a microswitch 7 interlocked with the latch 9 is opened momentary to reset the displacement measuring device as will be described later.

Then, the rubber sample 22 is mounted on the table 14 and raised by a dial wheel 16 until its surface 21 engages the bottom surface 21 of the casing, thus completing preparation of the measurement.

The measurement is commenced by depressing push button 2 for releasing the needle holder 30. Then, the needle 1 is forced against the sample 22 by the force of spring 12 and the displacement of the needle accompanies a vibration which is attenuated by the action of the spring and the damping action of the sample rubber so that the needle reaches a steady state in a relatively short time. The displacement of the needle is converted into an electric signal by the transducer described above and the signal is sent to a displacement measuring device to be described later.

When the push button 2 is depressed to disengage the latch 9 from projection 4, microswitch 7 is closed to send a measurement start signal to the displacement measuring device. The measuring time is measured starting from this instant thereby enabling to measure the displacement of the needle at any time by the displacement measuring device. Alternatively, it is also possible to measure the maximum displacement without considering the time.

Turning now to FIG. 4 showing one example of the displacement measuring device, the displacement measurement is started by depressing push button 2. Concurrently therewith, the microswitch 7 sends a signal which is used as a trigger signal for the measuring device and its waveform is shaped by a waveform shaper 53. The output thereof is converted into a pulse having a definite width T by a pulse generating circuit 55. This pulse is used to start an analogue-digital converter 56 when time T elapses after commencement of the measurement, the time T being set by the regulation of JIS, ASTM or DIN. As above described, the displacement of the needle is detected as an electric signal by the electric transducer comprising a combination of magnetic member 10 and coil 11 or a Hall element and a magnetic member and the signal is amplified and rectified by a circuit 51 and then applied to a peak dector 52 via a transfer switch 59. The peak detector 52 is constructed to detect and hold the maximum value and by sampling the same at a proper time the maximum value of the displacement can be determined as prescribed by ASTM. When transfer switch 59 is thrown to the lower side for applying the output from circuit 51 to analogue-digital converter 56 and when the output is sampled at a proper time, the value prescribed by JIS, ASTM or DIN can be measured. The analogue-digital converter 56 operates to convert the electric signal representing the displacement into a digital signal for displaying the displacement by digits or for operating other device, for example an automatic tension testing machine, not shown. As described above, the analogue-digital converter 56 is started by the pulse generated by the pulse generating circuit 55 for sampling the displacement signal at a prescribed time of said regulations of various countries. The digital signal obtained in this manner is supplied to the other device described above or converted by a display converter 57 into a form suitable to be displayed by a digital display device 58 which may take the form of a neon tube, a liquid crystal display unit or a luminous diode.

Upon completion of the measurement, a reset button 54 is depressed for resetting the peak detector 52 for preparing it for the next measurement. It is also possible to mount a microswitch acting as a reset switch on lever 3 shown in FIG. 1.

It is possible to convert into an electric quantity representing the hardness of rubber the displacement at any time among the displacements thus determined by using time as a parameter or the maximum displacement, by suitable method well known in the art.

It will be noted that the invention provides novel apparatus for measuring the hardness of rubber at high accuracies.

We claim:

1. Apparatus for measuring the hardness of rubber of the type wherein a needle is urged against the surface of a rubber sample and the degree of penetration of the needle is determined for measuring the hardness, said apparatus comprising driving means for urging said needle against the surface of said sample under a substantially constant speed and force, said driving means including spring means for driving said needle, a lever for causing said needle to store energy in said spring means, releasable latch means for latching said needle in a position in which the spring means is storing energy and for releasing said needle to cause said spring means to urge the needle against the surface of said sample, an electric transducer for detecting the degree of penetration of said needle into said sample thereby producing an electric signal corresponding to the displacement of said needle, an electric circuit for processing said electric signal, switch means which generates a signal when said needle is released, said signal being applied to said electric circuit for determining the starting point of the time necessary to measure said displacement, said electric circuit comprising a rectifier for rectifying the electric signal generated by said electric transducer, a peak value detector for detecting the peak value of the output of said rectifier, an analogue-digital converter for converting the output of said rectifier into a digital quantity, a pulse generator responsive to the signal generated by said switch means for producing a pulse signal which is applied to said analogue-digital converter, and digital display means connected to display said digital quantity.

* * * * *